United States Patent [19]

Denyer

[11] Patent Number: 5,533,501
[45] Date of Patent: Jul. 9, 1996

[54] NEBULISER

[75] Inventor: John S. H. Denyer, Sussex, England

[73] Assignee: Medic-Aid Limited, Sussex, England

[21] Appl. No.: 251,922

[22] Filed: Jun. 1, 1994

[30] Foreign Application Priority Data

Jun. 4, 1993 [GB] United Kingdom .................. 9311614

[51] Int. Cl.⁶ .......................... A61M 11/00; A61M 16/00
[52] U.S. Cl. ................. 128/200.21; 128/200.14; 128/200.18; 128/203.12; 239/338
[58] Field of Search .................. 128/200.18, 200.21, 128/203.12, 200.22, 200.24, 204.13, 200.14; 239/338, 370, 432

[56] References Cited

U.S. PATENT DOCUMENTS

| Re. 23,642 | 7/1991 | Lester | 128/200.21 |
|---|---|---|---|
| Re. 33,717 | 10/1991 | Svoboda | 128/200.21 |
| 992,156 | 5/1911 | Brousseau | 239/432 |
| 2,670,739 | 7/1951 | McNeill | 128/200.18 |
| 4,251,033 | 2/1981 | Rich et al. | 239/338 |

FOREIGN PATENT DOCUMENTS

3429411  2/1987  Germany .

*Primary Examiner*—Edgar S. Burr
*Assistant Examiner*—V. Srivastava
*Attorney, Agent, or Firm*—Nixon & Vanderhye

[57] ABSTRACT

An effective nebulizer atomizes fluids or powders carried in a stream of pressurized gas. The nebulizer includes a casing, a nozzle head having at least one gas outlet and a reservoir disposed around the at least one gas outlet for receiving the substance to be atomized, and from which the substance is atomized by the steam of gas. The substance to be atomized is introduced into the nebulizer, at least two holes opening into the reservoir through which the substance to be atomized is drawn by the stream of gas issuing from the at least one gas outlet. Also provided is an airflow control device having a bridge bar which is locatable for interception of the gas issuing from the at least one gas outlet so as to be freely angularly displaceable for deflecting the stream of gas issuing from the at least one gas outlet across the reservoir.

19 Claims, 7 Drawing Sheets

PRIOR ART

Fig.1.

PRIOR ART

NEBULISER

BACKGROUND AND SUMMARY OF THE INVENTION

The present invention relates to atomizers and nozzles for atomizers used for atomising fluids or powders carried in a stream of pressurised gas. The invention is particularly useful for introducing a medicament in the form of a medicinal fluid or powder into gas for inhalation by a patient, thereby administering a medicine to the patient. The substance may typically be a powder, a liquid or a particulate suspension. German Patent Specification DE 34 29 411 describes a nozzle for atomising, distributing and mixing fluid or powdery substances by means of a stream of gas and, in particular for producing aerosols for the purposes of inhalation. More specifically claim 1 of DE 34 29 411 claims such as a nozzle consisting of a nozzle body and an airstream control device which can be mounted on the nozzle body, wherein the stream of pressurised gas emerging centrally from the head of the nozzle through a pressurised gas duct draws in the material to be atomised from two intake ducts which are adjacent the pressurized gas ducts and are diametrically opposite one another, and wherein the airstream control device comprises a rebound bar in the outlet cone of the pressurized gas which bar is connected to a ring which can be mounted on the head of the nozzle body and is characterized in that the rebound bar (11) is shaped as a wedge in a manner known per se on its side opposite the nozzle opening (29);

in that two parallel guide surfaces (15) are provided on the ring (14) and corresponding guide surfaces (17) which are adapted to the first guide surfaces and are aligned therewith are provided on the nozzle head (16) in such a way that, when the airstream control device is mounted, the rebound bar (11) extends transversely to the connection line between the outlet openings (30, 31) of the intake ducts (5, 6);

that the outer contour of the ring (14) of the airstream control, device (3) projects over the edge of the nozzle head (16) on al sides.

Figure 1:
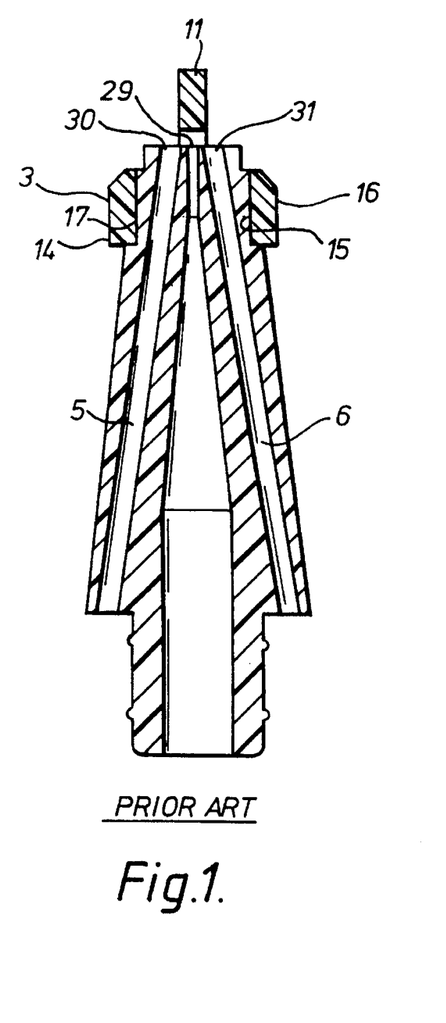
FIG. 1 shows a sectional view of a nozzle head according to prior art reference DE 3429411.
Figure 2:
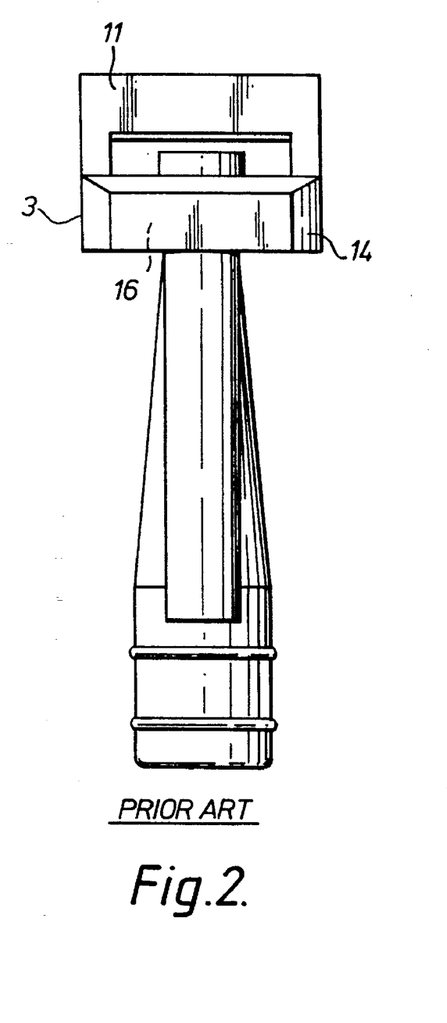
FIG. 2 shows another view of prior art reference DE 3429411.
Figures 3, 4:
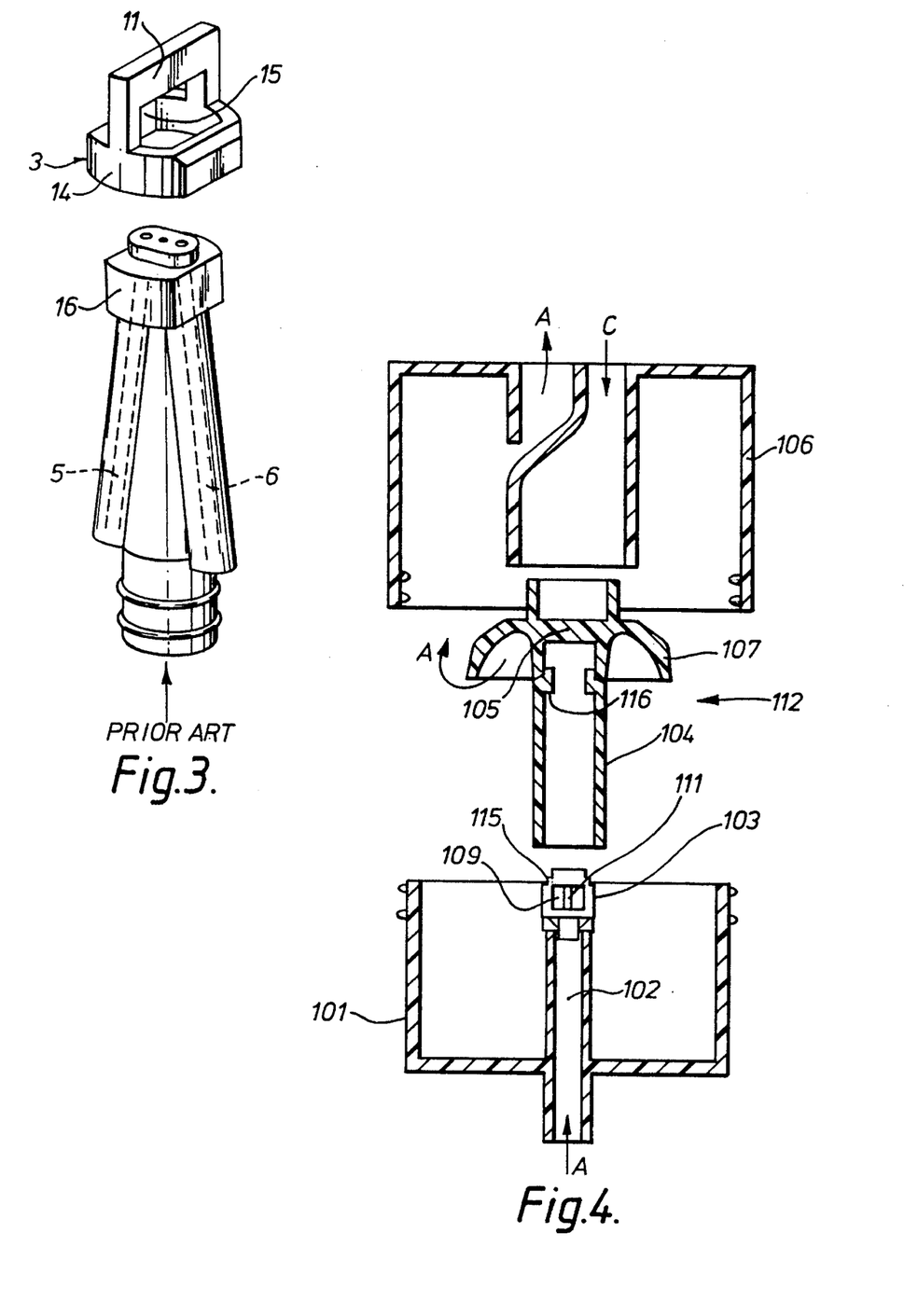
FIG. 3 shows a perspective view of prior art reference DE 3429411.
FIG. 4 shows an atomizer of the present invention all of which is shown in exploded cross-section except the nozzle head which is shown unsectioned.

For reference, copies of FIGS. 1, 2 and 3 of DE 3429411 are illustrated in FIGS. 1 through 3 of the drawings indicating those components mentioned above and bearing reference numbers (11), (29), (15), (14), (17), (16), (30, (31), (5), (6) and (3).

Accurate alignment of the rebound bar is vital to the correct function of such a conventional atomizer as described in DE 34 29 411.

There are several disadvantages to the atomizers that have been used hitherto. The atomizers are often used by elderly or infirm people who meet occasionally take the atomizer apart for cleaning. When re-assembling the atomizer, the person must take care to locate the ring or tube correctly so that the rebound bar is in correct alignment as indicated above. There are usually only one or two correct orientations which will permit the device to function properly. If the atomizer is incorrectly assembled then it will not function correctly, since the bar will not correctly divert the stream of gas from the nozzle head.

Our investigations have shown that it is unnecessary to form parallel guide surfaces (15) on the ring (14) and corresponding guide surfaces (17) on the nozzle head (16) for the purpose of positioning the rebound bar (11) transversely to the connection line between the outlet openings (30, 31) of the intake ducts (5, 6).

Such a structure complicates production of moulding tools and increases not only the cost of the tooling but also the cost of the finished product.

According to one form of the present invention, a nebuliser the atomising a substance entrained into a stream of gas includes a casing, a nozzle head having at least one gas outlet and a reservoir disposed around said at least one gas outlet for receiving the substance and from which the substance is atomised by the stream of gas, means for introducing the substance to be atomised into the nebuliser, at least two holes opening into the reservoir through which the substance to be atomised is drawn by the stream of gas issuing from said at least one gas outlet and an airflow control device having a bridge bar which is locatable for interception of the gas issuing from said at least one gas outlet so as to be freely angularly displaceable for deflecting the stream of gas issuing from said at least one gas outlet across the reservoir.

Preferably the angularly displaceable airflow control device includes a tubular carries which fits on and around the nozzle head to support the bridge bar and which further includes spacing means for positioning the bridge bar in a spaced relationship relative to the reservoir and said at least one gas outlet.

It is advantageous to have as many holes leading to the reservoir a possible. This improves the flow of the substance to the reservoir. Four holes have been found to give a satisfactory flow of the substance whilst keeping the manufacturing cost down.

Preferably the nebuliser includes a source of the substance to be atomised in the form of a container.

It will be appreciated that where the reservoir is annular, the angular position of the diametrically supported rebound bar is irrelevant since it is always disposed diametrically across the reservoir and in line with the pressurized gas outlet.

BRIEF DESCRIPTION OF THE DRAWINGS

Embodiments of the present invention will be described hereinafter by way of example only with reference to the drawings in which.

DETAILED DESCRIPTION OF THE DRAWINGS

Figure 12:
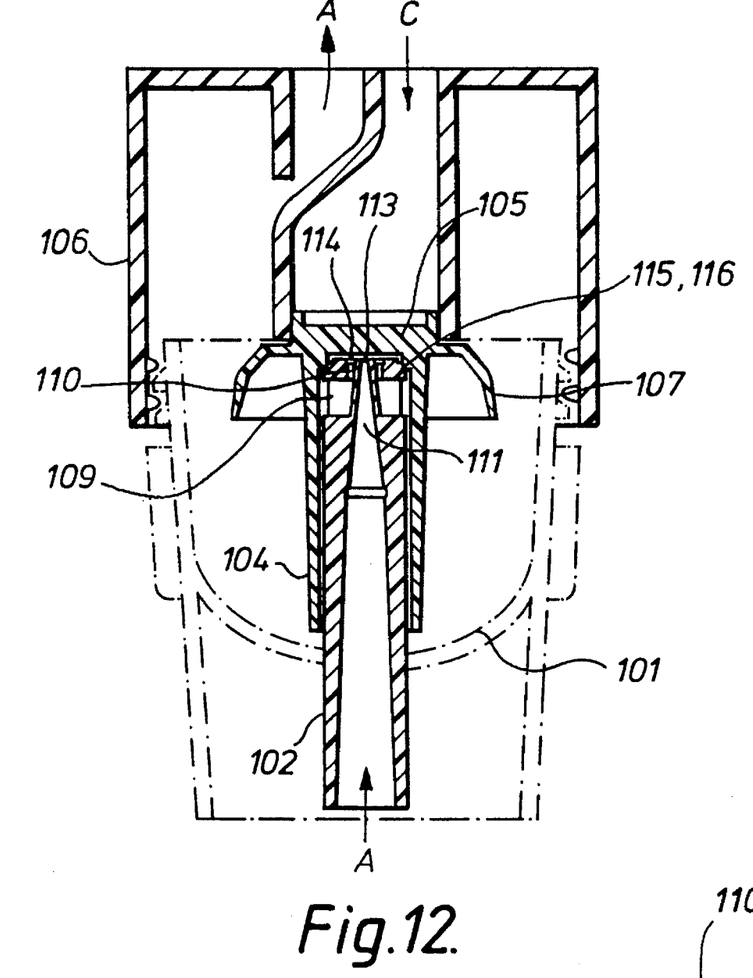
FIG. 12 shows a sectional view of the nebuliser in its assembled state.
Figure 13:
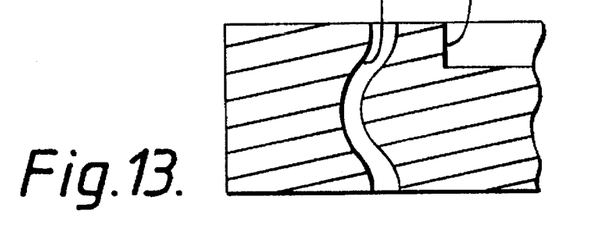
FIG. 13 is a detail sectional view showing a modified form of the shape of the holes through which the substance to atomized is drawn may take.

FIGS. 4 and 12 show an atomizer in which a gas duct (102) leads gas into the atomizer through a primary container (101). The container (101) contains a substance to be atomised into the gas. A lid (106) fits onto the container (101) in an airtight manner. In this embodiment, the lids screws onto the reservoir body.

Figure 5:
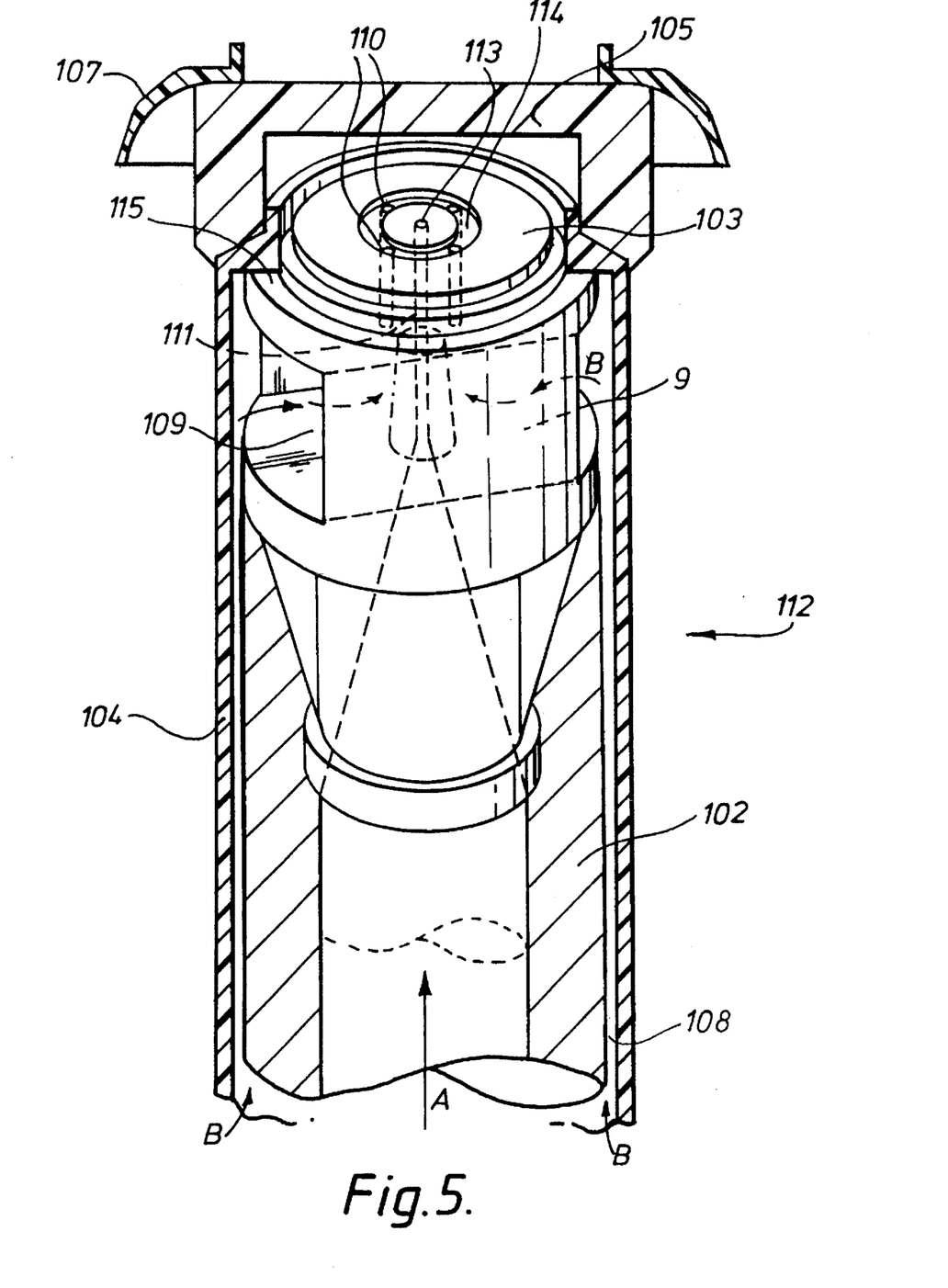
FIG. 5 shows a part cross-sectional—part perspective view of the atomizer according to the present invention.
Figure 6:
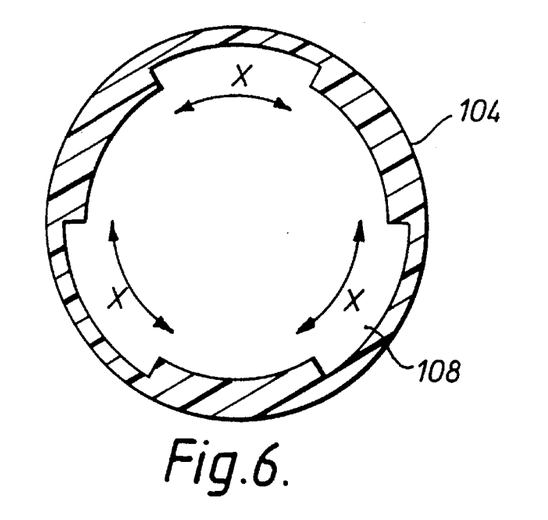
FIG. 6 shows a sectional view through the baffle tube of the present invention.
Figure 7:
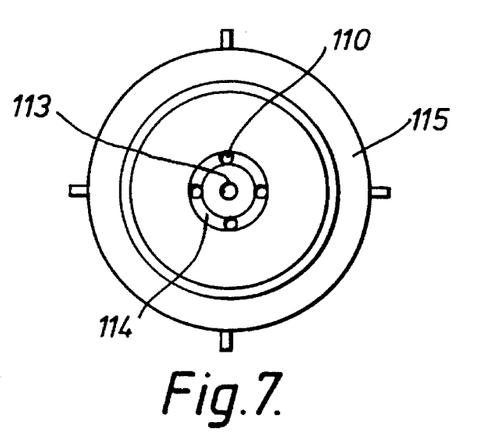
FIG. 7 shows a plan view of the nozzle head of the atomizer according to the present invention.
Figure 8:
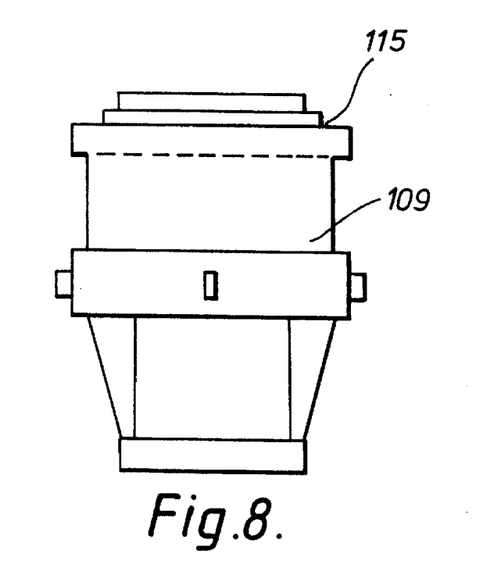
FIG. 8 shows an external view of the nozzle head before being moulded into the gas duct.
Figure 9:
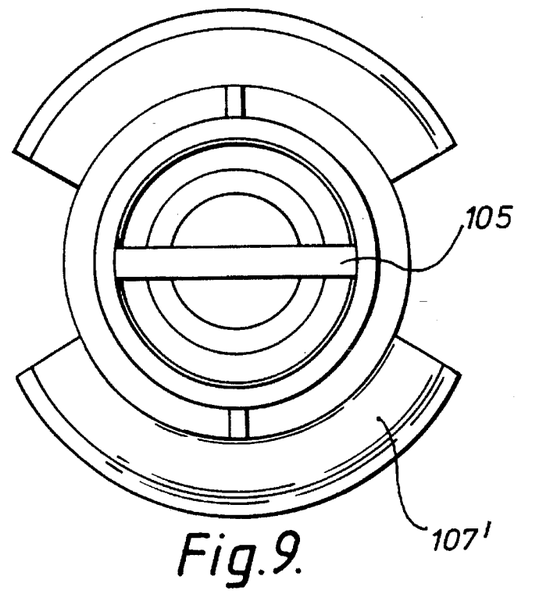
FIG. 9 shows a plan view of a baffle with two portions removed.
Figure 10:
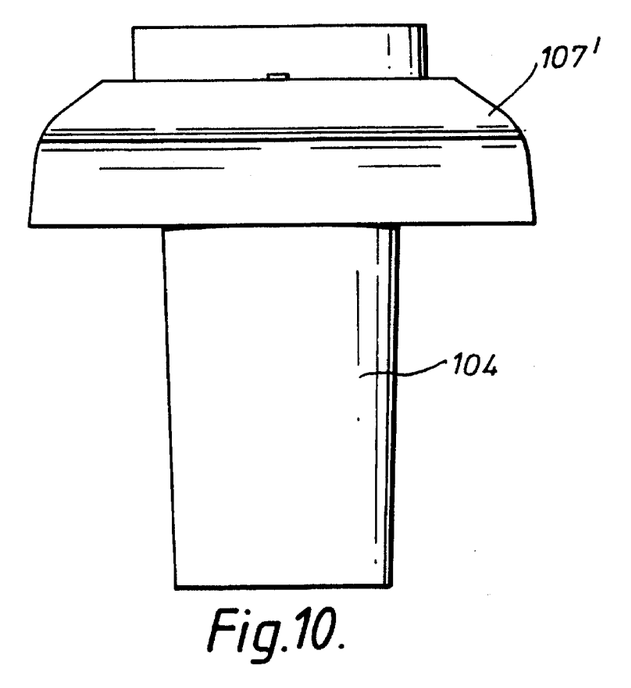
FIG. 10 shows a side view of the baffle with two portions removed from the mushroom portions.
Figure 11:
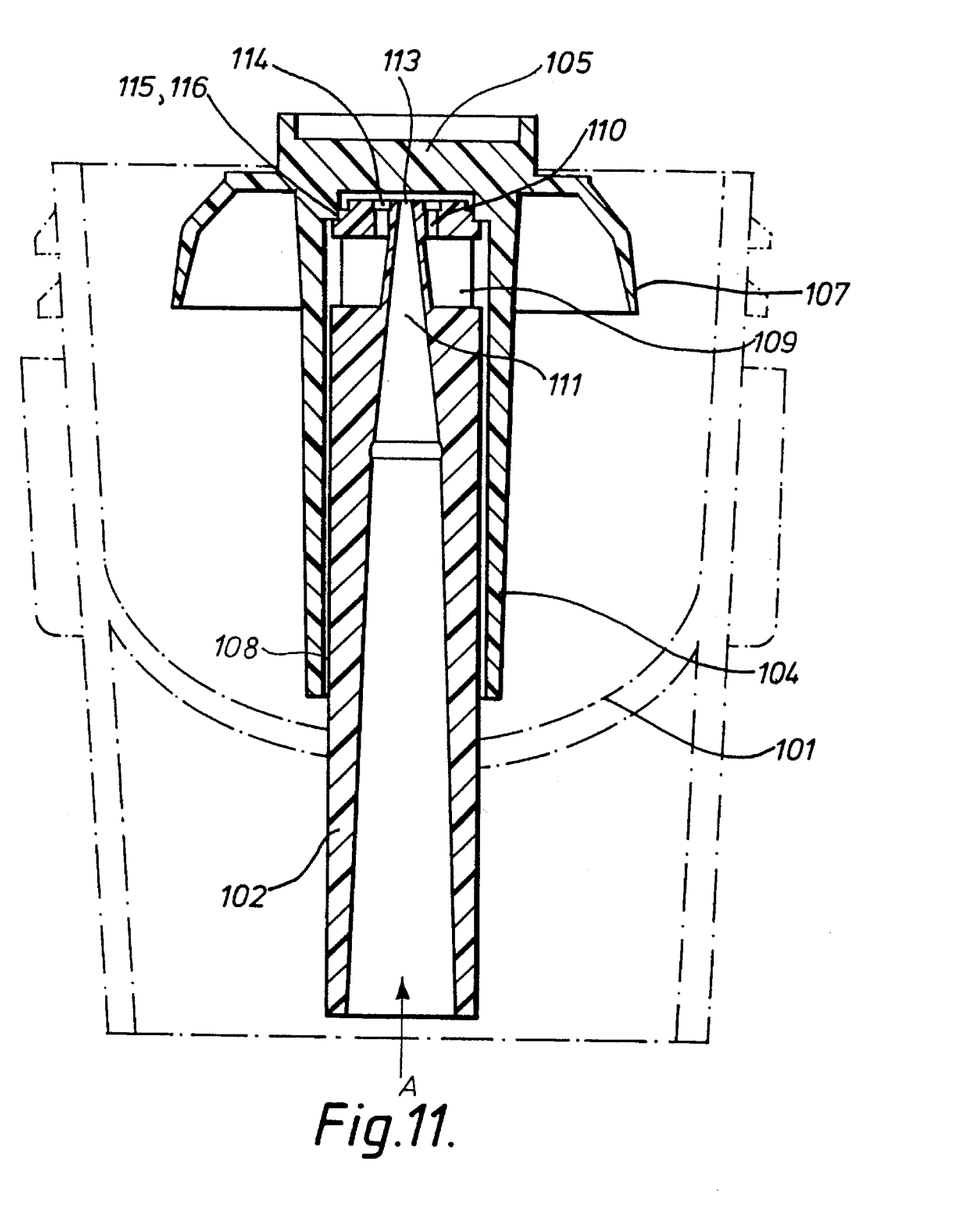
FIG. 11 shows a sectional side view of the baffle assembly and base portion.

A nozzle head (103) is seated on the top end of the gas duct (102). The gas duct (102) is preferably moulded around the nozzle head (103) so that the head is not removable. The nozzle head (103) has a transverse gallery (109) which extends across the full width of the nozzle head (103). The nozzle head (103) also includes a gas connection tube (111) which leads gas from the gas duct (102) out through the top of the nozzle head (103) to a gas outlet (113). The gas connection passage (111) is visible in FIG. 4 as it passes through the transverse gallery (109). In the upper surface of the nozzle head (103) an annular groove is formed which encircles the gas outlet (113). This groove forms a reservoir (114) (See FIGS. 5, 7, 11 and 12) which, in use, contains a quantity of the substance to be atomised. At least two holes (110) lead from the gallery (109) to the reservoir (114). The gallery 109 may have two open ends as seen in FIG. 5 and through which the substance to be atomized flows as indicated by arrows B is FIG. 5. As pressurized gas leaves the head (103) through the gas outlet (113), the substance contained in the reservoir (114) is atomized into the stream of air. This also causes more of the substance to be drawn into the reservoir (114) from the gallery (109) through the holes (110). The mechanism by which atomization and filling of the reservoir (114) takes place will be explained below. The nozzle head (103) also includes one or more shoulders (115) around the top of the head (103).

A freely rotatable baffle assembly (112) fits over and around the nozzle head (103) and the gas duct (102). The baffle assembly (112) includes a baffle tube (104) which fits around the nozzle head (103) and gas duct (102), a bridge bar (105) which sits above the nozzle head (103), and a mushroom baffle (107) which directs the pressurized air and atomised substance downwards before they can escape through an outlet in the lid (106). The baffle tube (104) slides over the nozzle head (103) and gas duct (102) and reaches almost to the bottom of the container (101). The inside of the baffle tube (104) contains one or more steps (116) positioned to engage with the shoulders (115) of the nozzle head (103). The baffle assembly is thereby supported by the nozzle head (103). The steps (116) seat on the shoulders (115) to form a seal. When seated on the nozzle head (103), the baffle assembly (112) locates the bridge bar (105) directly across the path of the stream of air which passes out from the gas connection tube (111) of the nozzle head (103) and diametrically across the annular reservoir (114).

The mushroom baffle (107) extends outwardly from the baffle tube (104) and slopes towards the primary reservoir (101) the further it extends from the baffle tube (104). Part of the mushroom baffle (107) projects upwardly and fits into an inlet chimney in the lid (106). If desired, the mushroom baffle may simply abut against the lower end of the inlet chimney. In some circumstances, the droplets or particles which enter the stream of gas are too large, and so the lower surface of the mushroom baffle directs them downwards back into the container. The large droplets gather on the underside of the mushroom baffle before running to the edge and dropping back into the container. As the gas exits from the gas outlet (113) in the top of the nozzle head (103) it is diverted by the bridge bar (105) so that it is directed across the reservoir (114). The airflow through a nebuliser is usually controlled externally. For example, in order to administer a medicine to a patient, the atomised substance must be put into the inhaled air. The patient's inhaled air is directed through the nebuliser before entering the patient. Air (C) is drawn into the nebuliser through the inlet chimney in the lid (106). This air meets the emerging gas from the gas outlet (113). The emerging gas causes atomization of the substance, and these atomised particles are then carried away by the inhaled air (A). The atomised substance is directed downwards by the mushroom baffle (107). The passage of the gas over the reservoir (114) atomises the substance to be atomised, carries the substance away and draws more of the substance into the reservoir (114). The air passes downwards, under the influence of the mushroom baffle. Oversize particles are collected on the underside of the mushroom baffle (107). The air then passes over the upper surface of the mushroom baffle (107) and leaves the atomizer through an outlet in the lid (106).

The lid (106) fits onto the container body (101) and holds the baffle assembly (112) securely in place on the nozzle head (103) thereby forming a seal between the nozzle head and the baffle.

The baffle assembly (112) of the present invention does not require seating against the nozzle in any one angular position. Since the baffle assembly (112) is freely angularly rotatable on the nozzle head (103), it may be seated in any orientation as long as the step (114) is seated on the shoulder (115). The bridge bar (105) is, therefore, freely angularly displaceable in line with the gas outlet. This arrangement is therefore an improvement over the prior art because it is much easier to reassemble, in that it is not necessary to position the baffle assembly in one particular position. The feature which is very important considering the elderly or infirm patients who must use it.

FIG. 5 shows a sectional view of the assembled gas duct (102), nozzle head (103) and baffle assembly (112). The gas duct (102) is moulded around the nozzle head (103) to attach the nozzle head to the gas duct (102). The nozzle head (103) is shaped with various external features such as flanges in order that once the gas duct has been moulded around the nozzle head (103), the two may not be separated. The gas (A) passing up the gas duct (102) enters the head (108) and passes through the gas connection tube (111). The gas leaves the head (103) through a gas outlet (113) in the top of the head. Encircling the gas outlet (113) is the annular groove in the top of the head (103). This annular groove forms the reservoir (114). Around the gas outlet (113) and disposed within the reservoir (114) are a number of holes (110), in this case four, but there must be at least two which lead the substance to be atomised from the transverse gallery (109) to the reservoir (114). The holes (110) are equally spaced from each other. The bridge bar (105) of the baffle assembly (112) is disposed across the stream of gas, thereby acting as a gas flow control surface. Bridge bar (105) is mounted by the tubular carrier/baffle tube (104). Because there is a reservoir (114) all the way around (surrounding) the gas outlet (113), it does not matter in what orientation the bridge bar (105) lies across the gas outlet (113). The stream of gas emerging from the nozzle head (103) is divided by the bridge bar so that it flows over the reservoir. The gas draws the substance to be atomised through the noise (110) thereby filling the reservoir (114). As a result of the substance being drawn through the holes (110), a flow of the substance occurs following arrows B. The substance is held in the container (101) from where it flows between the outer surface of the gas duct (102) and the inner surface of the baffle tube/tubular carrier (104). The substance then enters the gallery (109) from each end. Once the gallery (109) is filled with the substance, the substance passes through the holes (110) into the reservoir (114) of the nozzle head (103) and into the stream of gas.

FIG. 6 shows a section through the baffle tube (104). Three longitudinal grooves (108) run up the inner surface of the baffle tube (104) forming supply passages up which the substance to be atomised passes. The three grooves (108) are evenly spaced, and all are of the same angular width X. The baffle tube (104) in which the grooves (108) are located is part of the baffle assembly (112). The tube (104) is, therefore, rotatable about the axis passing through the longitudinal center of the tube (104). It is desirable that the channels formed by the grooves (108) always align with the openings into the transverse galley (109), so that the substance may always pass from the container (101) shown in FIG. 4 to the gallery (109) shown in FIG. 5. To ensure this, the grooves are wide enough that no matter what angular position the baffle tube (104) is in, the substance to be atomised is always able to enter the gallery. Preferably, the substance should always enter the gallery from both ends. If the substance is always to enter the gallery from both ends, the part of the tube (104) between the grooves must be narrower than the width of the gallery (109) at each end.

FIG. 7 shows a plan view of the nozzle head. The central hole is the gas outlet (113) of the gas connection passage. Disposed equiangularly around the gas outlet (113) are four holes (110) from which the substance to be atomised is drawn. These holes (110) are disposed in the annular groove which forms the reservoir (114) around the gas outlet (113). The nozzle head also includes a shoulder (115) running around the top of the nozzle head (103) on which the baffle assembly (112) is rotationally seated.

FIG. 8 shows the nozzle head (103) before being moulded into the gas duct (102). The gallery (109) is shown by dotted lines. The gallery (109) is open at each end. The shoulder (115) may be seen, on which the baffle assembly is seated. This seat preferably forms a seal.

FIGS. 9 and 10 show a baffle assembly (112) which has a slightly different mushroom baffle (107'). Since the stream of pressure gas is divided by the bridge bar (105), two streams of pressure gas pass radially across the reservoir (114) in opposite directions. Both streams of gas are directed downwardly and around the mushroom baffle (107') but at diametrically opposed sides of the mushroom baffle (107'). The streams of gas only meet part of the mushroom baffle (107') the rest having no purpose. These sections of the mushroom baffle (107') which do not direct gas downwards may be omitted, as in this embodiment, which assists in atomization and helps to equalize pressure in the region of the bridge bar (105).

In other embodiments of this invention, several variations may be made. For example, the gallery (109) nee not be a single gallery (109) across the head, but may be a double or triple gallery. Each gallery would cross the other gallery or galleries forming a cross shaped, or a star shaped gallery with four or six or more open ends to the galleries.

FIG. 11 shows the baffle assembly (112) according to the main embodiment of the invention seated on the nozzle head (103). The gas (A) passes up the gas duct (102) and through the gas connection tube (111) in the nozzle head (103). As the gas exits from the top surface of the nozzle head (103) through the gas outlet (113), it is divided by the bridge bar (105). The gas is directed over the reservoir (114) where the substance is atomised. The gas then meets a flow of air which is being inhaled by a patient, and together the air, gas and atomised substance are directed downwards by the lower surface of the mushroom baffle (107) and back up around the mushroom baffle (107) to an outlet in the lid (106). The substance to be atomised is drawn from the container (101), along grooves (108) between the gas duct (102) and the baffle tube (104),—see also FIG. 3 and into the transverse gallery (109). From the gallery (109), the substance passes through the holes (110) into the reservoir (114).

The number of grooves corresponding to grooves (108) (see FIG. 6) opening into the inner surface of the baffle tube (104) may vary. For example, five grooves may be used and, if a double or triple gallery is used, then five or seven grooves (108) may be much more suitable.

Furthermore, the grooves (108) may be positioned on the outer surface of the gas duct (102) so that the grooves (108) lead directly to the ends of the gallery or galleries. In that situation, the inner surface of the baffle tube (104) may be free of grooves.

In other embodiments, the number of holes (110) surrounding the gas outlet (113) may vary from three upwards. Four has been found to give excellent results.

Furthermore, it may be possible to improve atomization by shaping the holes (110). For example, the holes (110) may run helically through the nozzle head (103), or to be otherwise curved as shown for holes (110') in FIG. 13, in order to increase turbulence in the flow of the substance to be atomized.

I claim:

1. A nebuliser for atomising a substance to entrain it into a stream of gas, said nebuliser comprising:

a casing, a nozzle head disposed within said casing and having at least one gas outlet and an open reservoir surrounding said at least one gas outlet and for receiving a substance to be atomised and from which the substance is atomised by a stream of gas passing through said gas outlet, at least two holes opening into the bottom of the reservoir through which the substance to be atomised is drawn by the stream of gas issuing from said at least one gas outlet;

an airflow control device having a bridge bar which is mounted to intercept the gas issuing from said at least one gas outlet, said bridge bar being freely angularly displaceable with respect to the reservoir to deflect the stream of gas issuing from said at least one gas outlet across the open reservoir; and wherein the nozzle head includes a transverse gallery through which the substance to be atomized is supplied to said at least two holes.

2. A nebuliser according to claim 1 wherein the airflow control device includes a tubular carrier which fits on and around the nozzle head to support the bridge bar so that said bridge bar is angularly displaceable.

3. A nebuliser according to claim 2 wherein the nozzle head is mounted at an end of a gas duct which passes through a container for carrying the substance to be atomised, and the tubular carrier extends downwardly and around the gas duct to the bottom of the container.

4. A nebuliser according to claim 1 wherein the substance to be atomised is drawn into the transverse gallery from between an outer surface of the nozzle head and an inner surface of the tubular carrier.

5. A nebuliser according to claim 4 including three longitudinal grooves disposed in at least one of the outer surface of the nozzle head and the inner surface of the tubular carrier.

6. A nebuliser according to claim 4 including at least one longitudinal groove disposed in at least one of the outer surface of the nozzle head and the inner surface of the tubular carrier.

7. A nebuliser according to claim 6 wherein the substance to be atomised is drawn into the transverse gallery from said at least one longitudinal groove.

8. A nebuliser according to claim 6 wherein said at least two holes opening into the reservoir comprise four holes, and wherein said reservoir comprises an annular groove encircling said at least one gas outlet.

9. A nebuliser according to claim 5 wherein said at least one longitudinal groove is in alignment with at least one open end of the transverse gallery.

10. A nebuliser according to claim 1 wherein the transverse gallery has a plurality of ends; and wherein the gallery opens out of the nozzle head at one or more ends of the gallery.

11. A nebuliser according to claim 1 further comprising a container connected to said casing, said container containing the substance to be atomised, and said container in communication with said at least two holes opening into the reservoir.

12. A nebuliser according to claim 11 wherein the airflow control device includes a mushroom baffle which extends outwardly and downwardly from the region of the nozzle head serving to deflect oversize droplets of the substance back into the container.

13. A nebuliser according to claim 12 wherein the open reservoir comprises an annular groove encircling said at least one gas outlet.

14. A nebuliser according to claim 1 wherein the reservoir is an angular groove encircling the gas outlet.

15. A nozzle according to claim 1 wherein the said at least two holes are curved for inducing turbulence in the substance to be atomised as it is delivered to the reservoir.

16. A nozzle according to claim 1 including at least three holes opening into the reservoir through which the substance to be atomised is drawn by the stream of gas issuing from said at least one gas outlet.

17. A container as recited in claim 1 wherein said at least two holes opening into the reservoir comprises four holes.

18. A nebuliser according to claim 17 wherein the open reservoir comprises an annular groove encircling said at least one gas outlet.

19. A nebuliser according to claim 18 wherein said at least one gas outlet comprises a single gas outlet concentric with said annular groove.

\* \* \* \* \*